(12) United States Patent
Binder et al.

(10) Patent No.: US 7,297,128 B2
(45) Date of Patent: Nov. 20, 2007

(54) ARM SUSPENSION SLEEVE

(75) Inventors: William J. Binder, Beverly Hills, CA (US); Edward C. Leicht, Goleta, CA (US)

(73) Assignee: Gelzone, Inc., Richmond, VA (US)

( * ) Notice: Subject to any disclaimer, the term of this patent is extended or adjusted under 35 U.S.C. 154(b) by 617 days.

(21) Appl. No.: 10/829,867

(22) Filed: Apr. 21, 2004

(65) Prior Publication Data

US 2004/0260224 A1    Dec. 23, 2004

Related U.S. Application Data

(63) Continuation-in-part of application No. 10/334,201, filed on Dec. 31, 2002, which is a continuation of application No. 09/931,974, filed on Aug. 17, 2001, now Pat. No. 6,963,019.

(60) Provisional application No. 60/226,602, filed on Aug. 21, 2000.

(51) Int. Cl.
*A61F 5/00* (2006.01)
*A61F 13/00* (2006.01)

(52) U.S. Cl. ............... 602/62; 602/42; 602/48; 602/58; 602/75; 602/77

(58) Field of Classification Search ............ 602/4, 602/5, 20, 75–77, 79; 2/44, 45; 128/869, 128/877
See application file for complete search history.

(56) References Cited

U.S. PATENT DOCUMENTS

| 4,024,312 A | 5/1977 | Korpman ............ 428/343 |
| 4,166,464 A | 9/1979 | Korpman |
| 4,377,160 A | 3/1983 | Romaine ............ 128/156 |
| 4,671,267 A | 6/1987 | Stout ............ 128/156 |
| 4,675,009 A | 6/1987 | Hymes et al. ............ 604/304 |
| 4,838,253 A | 6/1989 | Brassington et al. |
| RE32,991 E | 7/1989 | Szycher et al. ............ 528/75 |
| 4,941,464 A | 7/1990 | Scott ............ 128/84 R |
| 4,991,574 A | 2/1991 | Pocknell ............ 128/156 |
| 5,156,601 A | 10/1992 | Lorenz et al. ............ 604/307 |
| 5,340,363 A | 8/1994 | Fabo |
| 5,419,913 A | 5/1995 | Podell et al. |
| 5,501,661 A | 3/1996 | Cartmell et al. ............ 602/58 |
| 5,540,922 A | 7/1996 | Fabo ............ 424/402 |

(Continued)

FOREIGN PATENT DOCUMENTS

EP    0 528 091 B1    2/1993

OTHER PUBLICATIONS

Int'l Search Report dated Oct. 29, 2003 for PCT/US03/01287.

(Continued)

*Primary Examiner*—Kim M. Lewis
(74) *Attorney, Agent, or Firm*—Clifford Chance US LLP

(57) ABSTRACT

A multi-layer wrap, for providing more comfortable gel treatment to skin while providing orthopedic support having a first layer of gel for contacting the skin and a second layer of an elastic and supportive loop portion of a hook and loop fastener, the wrap allowing for migration of moisture away from the skin. The wrap can be used as part of a suspension sleeve for use during arm surgery or post-operative recovery. The product is economically manufactured in the form of long rolls or as a sheet and is easily cut to any desired shape.

25 Claims, 14 Drawing Sheets

U.S. PATENT DOCUMENTS

| | | |
|---|---|---|
| 5,603,145 A | 2/1997 | Arakawa et al. .............. 24/442 |
| 5,635,201 A | 6/1997 | Fabo |
| 5,653,230 A | 8/1997 | Ciaglia et al. ......... 128/207.15 |
| 5,656,279 A | 8/1997 | Dillon ........................ 424/402 |
| 5,674,523 A | 10/1997 | Cartmell et al. ............ 424/445 |
| 5,759,560 A | 6/1998 | Dillon ........................ 424/402 |
| 5,843,018 A | 12/1998 | Shesol et al. ................. 602/79 |
| 5,891,076 A | 4/1999 | Fabo ............................ 602/52 |
| 5,895,656 A | 4/1999 | Hirshowitz et al. ......... 424/402 |
| 5,919,476 A | 7/1999 | Fischer et al. .............. 424/443 |
| 5,980,923 A | 11/1999 | Dillon ........................ 424/402 |
| 6,051,747 A | 4/2000 | Lindqvist et al. |
| 6,143,946 A | 11/2000 | Docter ........................ 602/41 |
| 6,194,629 B1 | 2/2001 | Bernhard |
| 6,207,875 B1 | 3/2001 | Lindqvist et al. |
| 6,506,175 B1 | 1/2003 | Goldstein |
| 6,520,926 B2 | 2/2003 | Hall |
| 6,963,019 B2 | 11/2005 | Binder et al. |
| 7,101,349 B2 | 9/2006 | Binder et al. |
| 7,112,183 B2 | 9/2006 | Binder et al. |
| 2006/0129081 A1 | 6/2006 | Binder et al. |

OTHER PUBLICATIONS

Upper Extremities, Silipos, vol. III, 1998 pp. 1-7.
Epi-Derm Silicone Gel Sheeting, State of the Art Treatment for Keloids and Hypertrophic Scars.
International Search Report dated Jun. 12, 2002 for PCT/US01/25715.
Partial EP Search Report for EP Application No. 01965969.7 dated Mar. 15, 2006.

ARM SUSPENSION SLEEVE

This is a continuation-in-part of co-pending application Ser. No. 10/334,201, filed Dec. 31, 2002, which is a continuation of Ser. No. 09/931,974 filed Aug. 17, 2001 now U.S. Pat. No. 6,963,019, which is a non-provisional application which claims the benefit of U.S. Provisional Application No. 60/226,602 filed Aug. 21, 2000.

BACKGROUND OF THE INVENTION

The present invention relates to a medical or surgical bandage suitable for use in providing musculo-skeletal support and treatment of skin conditions. More specifically, the present invention also relates to a sleeve suitable for suspending an arm during surgery.

During certain surgeries and post-operative recoveries, it is often necessary to hold a body part in a particular position for prolonged periods. The position may differ from the horizontal resting position of the operating table or hospital bed, requiring the use of a holding device. One particular case where holding a body part in a particular position is required is during arthroscopic surgery. In arthroscopic surgery, a small camera is inserted into the body close to a joint, like a shoulder, a knee, an elbow, a hip, an ankle or a wrist, to visualize the joint. Direct visualization of the joint greatly enhances the capability of the surgeon to elaborate a diagnosis of the joint problem with respect to other non-invasive techniques such as X-rays. During the same arthroscopic operation, other instruments can be inserted into the joint to correct the diagnosed problem under the visual guidance provided by the camera. Because of the characteristics of the procedure, it is necessary that the body parts around the joint are held in a steady, firm position, while allowing the surgeon to gain access to the parts of the joint. In shoulder arthroscopy, for example, the arm must be kept away from the body, so that the surgeon has better access to the shoulder joint. In addition, the joint must be placed at a particular angle so that the instruments the surgeon uses do not harm the nervous or vascular systems while penetrating the body.

Arthroscopic surgery has become a widely practiced surgical procedure, especially in sports medicine. Its advantages are its high diagnostic value and its lower invasiveness in comparison with other types of surgery, which considerably accelerates post-operative recovery time.

Keeping the joint in the correct position during the surgery is crucial for the success of the procedure. Nonetheless, it is important to avoid causing post-operative discomfort to the patient, which may happen due to the pulling force and compression that is applied for prolonged amounts of time during surgery.

There are a number of problems associated with currently available holding devices. First, they can often lead to post-operative patient discomfort due to the excessive compression used during surgery. Tight compression is used to prevent unintended movement of the body part during surgery. Also, when the device exerts a pulling force on the body part, it tends to hold it tightly by compressing the body part. Tight compression can potentially induce blood irrigation problems and/or bruising. Second, holding devices may use strong adhesives on the skin, leading to skin damage in some patients, especially in elderly patients. In some instances, the use of the prior art devices may not be possible because the patients have injured skin. Third, some holding devices may require complicated handling and/or storage because of their bulkiness. Fourth, some holding devices are comprised of several parts that must be inconveniently assembled prior to surgery. This lengthens unnecessarily the duration of the surgery, complicates production of the device, and increases the cost of surgery. Fifth, some holding devices require cumbersome customizing, which also unnecessarily lengthens the duration of the procedure, complicates use of the device, and again increases the cost of surgery. Sixth, some devices use abduction as the method of holding, which greatly limits the capability to mobilize and/or hold the body part in any desired direction. Seventh, some devices involve cylindrical wrapping, which typically applies too much pressure to the wrapped area, potentially leading to vascular circulation problems and unnecessarily complicates the assembly process.

SUMMARY OF THE INVENTION

The invention relates to positioning a gel against the skin utilizing a stretchable bandage that also provides the added benefit of orthopedic, or musculo-skeletal, support for the joint or portion of the body on which the bandage is wrapped.

More specifically, this invention relates to a multi-layered composite material comprising at least a layer of gel bonded to a stretchable carrier layer. In one embodiment, the stretchable carrier may comprise a firm and elastic loop portion of a hook and loop fastener. The stretch carrier layer is useful for positioning the gel layer in place on the body while at the same time providing substantial musculo-skeletal support to the portion of the body around which the bandage is wrapped.

One embodiment of this invention relates to a composite structure which incorporates the pressure therapy features of a firm yet stretchable carrier material with a silicone gel for treatment of skin conditions. Silicone gel materials are used in the medical field for the management of such conditions, for example, as dermal scarring, varicose veins and stasis ulcers. These silicone materials soften scar tissue and improve the cosmetic appearance of the scar tissue as well as the functional aspects of scars by reducing the constriction of scars and thereby enhancing mobility of the affected body part.

There is a need in the medical and veterinary fields to combine supportive (pressure) therapy with a gel treatment, particularly on the extremities of the body. In the case of veterinary applications, fur is used herein interchangeably with skin. Supportive pressure therapy is useful, for example, to provide musculo-skeletal support for joints and muscles, and in the treatment of carpal tunnel syndrome, arthritis and tennis elbow and aiding the musculo-skeletal system and skin in the prevention of injury caused by strenuous exercise and/or athletic activities. Other medical applications for this embodiment may include obstetrical and vascular support.

Obtaining combined gel treatment and pressure therapy is not easy or convenient under present methods. Typically in the medical and veterinary fields supportive pressure therapy is provided using compression garments or wraps. When used with a gel, a person must typically apply a layer of gel to the area of the body to be treated followed by wrapping another material such as a compression garment or wrap to keep the gel in position. The materials typically used don't provide the elastic support usually desired and therefore often require many turns of the material being wrapped around a body part or many efforts to wrap it properly. Excessive wrapping of a body extremity that includes many turns of a material around the same area will typically apply too much pressure to the wrapped area. Attempting to adjust the pressure exerted by a wrap that requires many turns is difficult and may require completely unwrapping and re-wrapping the area more than once to obtain the desired pressure. Any application of a wrap that exerts too much pressure to the area will often constrict or cut off the vascular circulation to the affected area and may adversely affect the treated area. Furthermore, typical materials lose much of their elasticity after only a couple of uses.

Hook and loop fasteners are now commercially available with firm yet stretchable loop portions of various thicknesses and a broad range of elastic properties. The elastic properties provided by the stretchable loop portion make it possible for a bandage using this material to be effectively wrapped as few as one turn around a part of the body while maintaining contact with the skin to be treated. By applying a surface layer of silicone gel to the flat side (non-loop surface) of a stretchable loop portion of a hook and loop fastener, it was discovered that bandages can be produced which provide a surface layer of silicone for uniform skin contact with the added benefit of musculo-skeletal support. The bandage, i.e. wrap, of this invention having a stretchable loop portion as the carrier layer for the gel can therefore follow the many shapes and anatomical contours of the body while at the same time providing secure positioning of the gel on the skin of the user. The characteristics of moisture wicking, which may be provided in the invention through, for example, surface imperfections, in combination with a gel layer and stretch carrier provide greater comfort to the user because the bandage allows for movement and flexing of the body without reducing effectiveness, i.e. support and resistance to slipping, while keeping the treated area dryer. Thus, the benefits provided by this invention offer the wearer of the bandage greater comfort and durability and makes for the ideal bandage for repeated usage and/or usage over long periods of time. In addition, this invention offers a beneficial combination of advantages for use in exercise and sports activities by simultaneously providing musculo-skeletal support, flexibility, comfort, ease of adjustment, and absorptive properties by absorbing sweat and by providing ventilation and/or moisture wicking to the treatment area.

One embodiment of this invention is an improvement over the prior bandages or wraps in that (a) the carrier material is firm and elastic providing substantial orthopedic support (i.e., musculo-skeletal support) with a limited number of wraps, (b) the product is far more durable than materials such as Lycra® and other known, thin elastic based products commonly available, (c) both pressure and silicone therapies may be applied concomitantly by this invention and therefore eliminating a separate and/or repeated process of fitting more than one material individually, and (d) patient compliance may be improved because continued and repeated, even long term, comfortable use of the product is possible without loss of support from the carrier material while in placement and in use, (e) the invention resists slippage, migration and unintended movement while in use, and, (f) the invention does not adhere to the skin nor does it significantly pull hair or fur when it is removed from use. Furthermore, the carrier of the present invention provides the added benefit of a bandage that supplies even pressure to the body across the area being treated. A strip of a complimentary hook portion of the hook and loop fastener provides quick and simple closure of the wrap about the body part while maintaining effective wrap placement even during strenuous activity and/or flexing of the body.

The manufacturing process of this invention lends itself to large-scale production in either flat sheets or long rolls. Final shapes of limitless configurations can then easily be cut from the sheets or rolls. This provides for rapid and cost effective production of custom-made shapes for any given application or patient.

A further embodiment relates to a medical or surgical arm sleeve, for use in securing an arm in a particular position during or after surgery. The sleeve can be used for suspending an arm during surgery, especially during arthroscopic surgery of the elbow or shoulder. Additionally, the sleeve can be used as part of a traction device to distend an elbow or shoulder joint during post-operative recovery. The sleeve encloses the arm with a wrap. The inner layer of the wrap is a gel, preferably a silicone gel, which is positioned against the skin, providing the adherence necessary during use to prevent slippage of the wrap independently of the arm position, while being gentle to the skin during use and removal. The lining gel is positioned against the skin utilizing a carrier, for example, a stretchable carrier. The wrap is secured around the arm with one or more closure strips, and then the wrapped arm is suspended by at least one fastener so that the tension between the structure from which arm is suspended and the rest of the body keeps the arm in a steady position. In one particular embodiment, at least a second fastener may be added to change or further modify and/or adjust the angle and position of suspension, by applying a pulling force on the arm in a perpendicular direction from the arm.

In some cases, such as after accidents where orthopedic injury and skin lesions have occurred, skin therapy may be convenient during post-operative recovery.

This arm sleeve is an improvement over the prior arm holding devices in that it does not cause post-operative patient discomfort due to the minimal yet effective compression it exerts on the arm. Therefore, no blood irrigation problems and/or bruising occur during or after its use. The sleeve does not cause skin damage nor discomfort during removal because the gel confers adherence to the skin during use without being adhesive. The sleeve is easy to store and handle because of its lightness. The sleeve can be used as a single unit, requiring no assembly at the time of wrapping the arm and shortening the duration of the procedure. The sleeve requires no or minimal customization, and if such is needed, it can be performed easily. The sleeve uses suspension for distending and/or holding the arm in place, providing the ability to move and hold the arm in any direction desired. However, the sleeve is also suitable for traction. The sleeve simplifies the suspension process because it is a single unitary longitudinal wrap and not a cumbersome cylindrical wrap. In addition, the sleeve allows the concomitant post-operative treatment of pre-existing skin conditions, abrasions and burns.

BRIEF DESCRIPTION OF THE DRAWINGS

FIG. 15(A) illustrates the view from the top, showing the arm resting on the gel layer 5 of the wrap, to which closure strips 80 are attached. Two part closure strips 80 show the hook surface 20 of the hook strip and the gel layer 5 of the loop strip. The arrow indicates the direction for folding the wrap over the top of the arm, using the distal end of the hand as a folding axis, so that the two ends of the wrap are in close proximity to the elbow. FIG. 15(B) is the bottom view of the arm shown in (A). It shows the uncovered elbow resting outside of the sleeve the closure strips 80 are attached to the loop surface 15 of the wrap. D-ring fastener 90 is attached to the longitudinal center of the wrap by means of distal pulling strip 95. From this view, two part closure strips 80 show the hook portion 20 of one strip, and the loop surface 15 of the other strip.

DETAILED DESCRIPTION OF THE INVENTION

Figure 1:
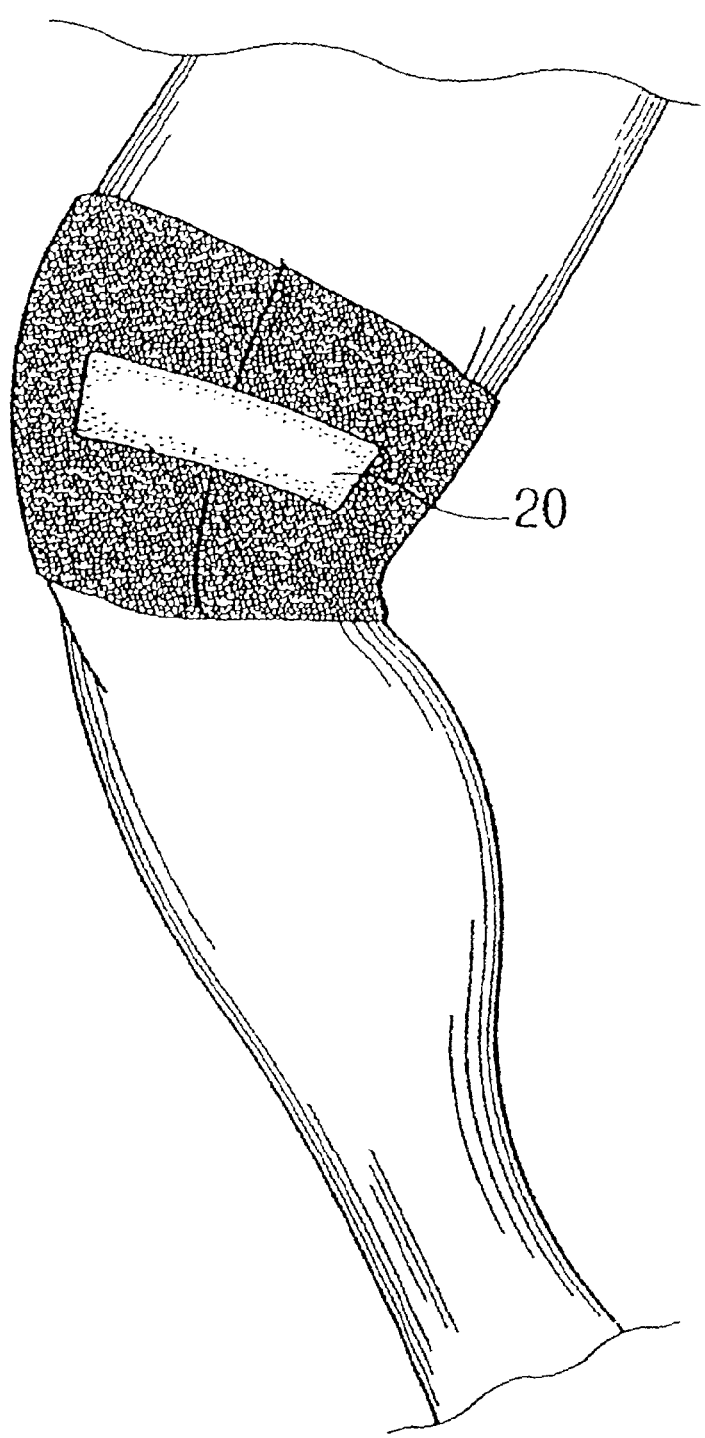
FIG. 1 is a perspective view illustrating the use of one embodiment of this invention on the knee of a user.
Figure 2:
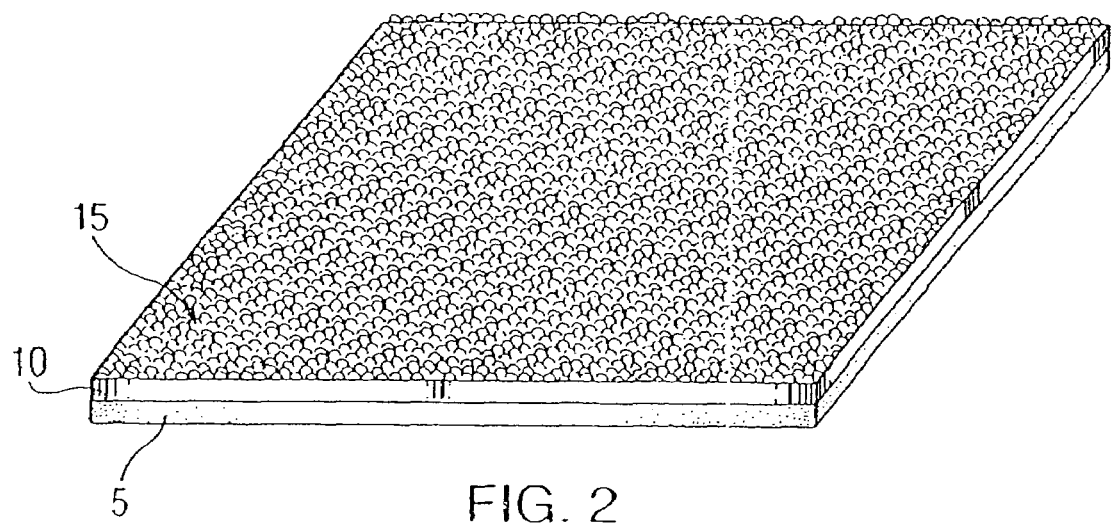
FIG. 2 is an embodiment illustrating gel layer 5 bonded to carrier 10 having loop surface 15.
Figure 3:
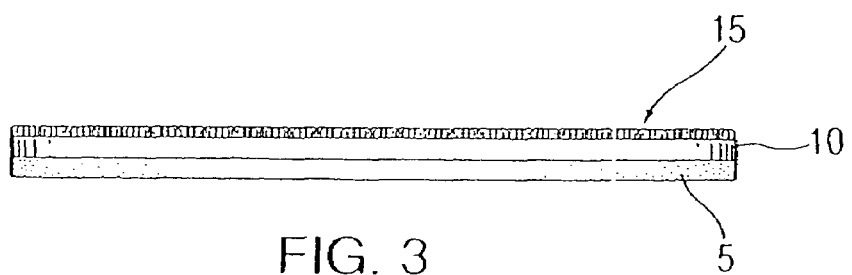
FIG. 3 illustrates carrier 10, having a loop surface 15, bonded to gel layer 5.
Figure 4:
FIG. 4 illustrates closure strip 20

The description provided below references FIGS. 1 through 21 as part of the disclosure and the associated reference numerals.

The device of the present invention, shown in FIGS. 1 through 3, 7 and 8, is generally described as a firm yet stretchable multi-layer bandage with a silicone gel coating 5 on one side. The carrier 10 is a thick, stretchable loop portion of a hook-and-loop fastener such as Velcro®. In a particular embodiment, carrier 10 is about ⅛ inch thick. The silicone gel used in gel 5 is commercially available as either a 1:1, 3:1, or 10:1 mixture of a polydiorganosiloxane resin and a catalyst. Generally speaking, the silicone gel is an addition cured polydimethyl-siloxane gel. This type of gel is well described in the literature, including some of the existing patent literature (e.g. U.S. Pat. No. 4,991,574 ("Pocknell") which is incorporated herein by reference). There is no particular reason to limit our device to silicone gel, if there are other gels that provide clinical benefit. Further, additives may be introduced into the gel, including, for example, oils, Ben-Gay™, and other topical medications and emoluments that seep into the skin area on which the gel is applied. Although other gels may be used, silicone gel has the special benefit of reducing the appearance of hypertrophic and keloid scarring. The advantages of silicone gel are widely known and are also well described in the existing patent literature (e.g. U.S. Pat. No. 5,759,560 ("Dillon"), U.S. Pat. No. 5,656,279 ("Dillon"), and U.S. Pat. No. 5,895,656 ("Hirschowitz et al.")) all the contents of which are herein incorporated by reference. Silicone gel is also known to be hydrophobic, so it won't break down or change characteristics in the presence of water or sweat. Cured silicone gel is cohesive (retains its shape) but is not very strong. It can be easily torn, and to be handled by the average person, it must be reinforced with some alternate carrier material.

In the present invention, carrier 10 is preferably a commercially available loop portion of a stretchable hook-and-loop fastener such as, for example Velstretch®. This "stretch" carrier is essentially the traditional loop portion of a hook-and-loop fastener woven with an elastic material. Depending on the degree of "stretch" desired, different elastic interweaves having various elastic properties and thicknesses may be used. For example, carriers which provide a stretch of approximately 50% in one or more directions may be obtained. This carrier, or substrate, provides the backbone, or compressive force, necessary to apply the silicone gel to any contour on the body, especially joints, both large and small, while also providing the benefit of support to the underlying tissue. The physical characteristics of the layers of the wrap allow the gel to stretch with the carrier fabric without the gel cracking or fracturing. The thickness of the carrier also provides support to the joint, so that the pain and discomfort of joint inflammation due to a variety of medical conditions is minimized. An added benefit of the carrier is to provide protection, for example, from abrasion, to the surface of the skin upon which the invention is applied. The support and protective aspects of the present invention, as described above, easily lend themselves to uses on animals as well.

Figure 7:
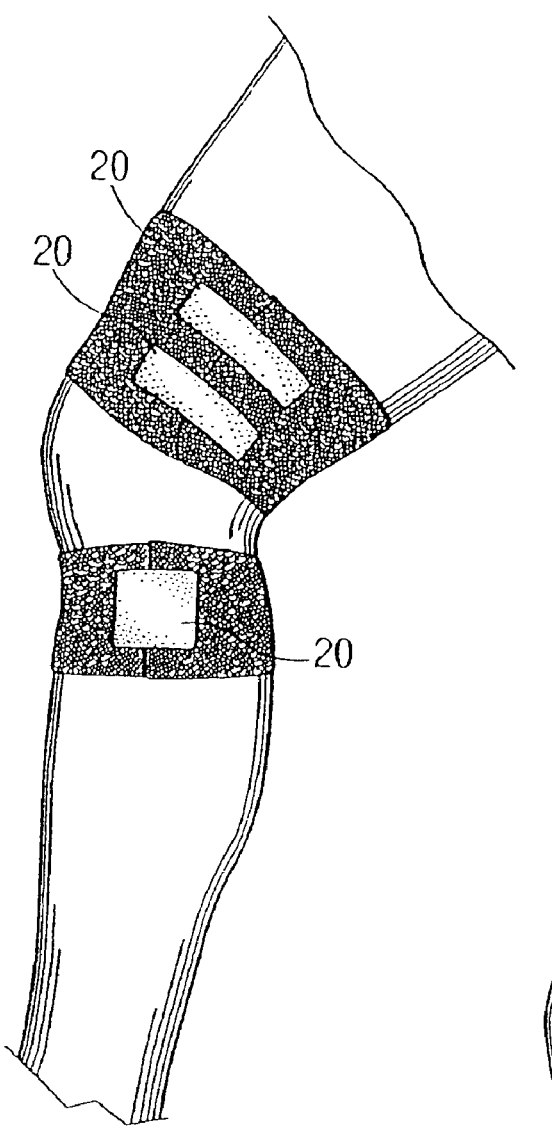
FIG. 7 is a perspective view illustrating the use of particular embodiments of this invention adjacent to the knee joint of a user.
Figure 8:
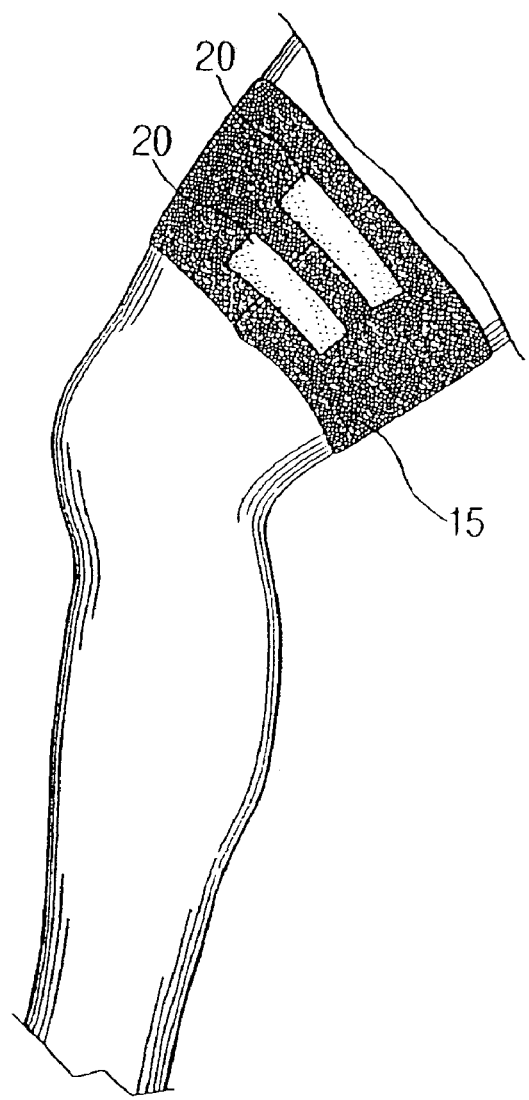
FIG. 8 is a perspective view illustrating the use of an embodiment of the present invention about the thigh of a user, and showing loop surface 15 of the bandage and closure strips 20.

In one embodiment of the present invention, the opposed surface of the "fuzzy" side or "loop" side 15 of the carrier 10 is used as the carrier for the gel. The bandage may be secured about the afflicted joint or area of the body with a complimentary strip of the hook portion 20 (FIG. 4) of a hook and loop fastener material which may be used to keep the bandage closed around the joint or area of the body. Multiple strips or one large strip of width equal to approximately the width of the bandage may also be used to provide proper securing of the bandage as shown in FIG. 7.

In a particularly preferred embodiment for skin treatment, the combined product of this invention has the "loop" side, or loop portion 15 (the soft side), of the stretch carrier 10 on one side and a layer of silicone gel on the other. The gel goes against the skin, and the product is fixed in place by wrapping the body portion with the bandage and applying a complimentary "hook" or closure strip 20 of fastener material at any point along the bandage seam.

Another embodiment of this invention could be provided in a roll form, about 3" wide by about 1 foot long for applications such as those currently employing use of an Ace® type bandage. In this configuration, the present invention can replace the application of Ace-type bandages for musculo-skeletal support and other orthopedic bandages which are specially configured to fit knees, ankles, wrists, elbows, and other problematic joints. Other dimensions applicable to specific applications are also contemplated, such as for use around a thigh or forearm.

For application to areas of the body that require longer lengths to make a wrap, the gel 5 may be applied only to a portion of a length of the carrier material. The gel layer may be provided in a size suitable to treat a desired skin condition only. For example, in the treatment of a scar resulting from a cessarian section operation, the gel portion may be sized only large enough to treat the scar itself, while the carrier 10 is of a length that permits wrapping the bandage around the torso of the person to support the gel in contact with the treatment area.

It is an embodiment of the present invention for the stretchable carrier 10 to provide a platform for the gel to be continuously applied against any existing scar, which will in turn provide the widely understood benefit of reduced scar appearance. Because the gel is deposited on the carrier 10 while the carrier 10 is in the un-stretched position, it should be understood that, as the carrier 10 is expanded, the gel also expands in the same direction. This will allow air to circulate into the treated area, reducing discomfort due to sweating, yet still provide the benefit of the gel applied against the scar. Further, as the carrier 10 is expanded and then closed using the hook section, the carrier 10 provides compression and support to the affected area.

Figure 9:
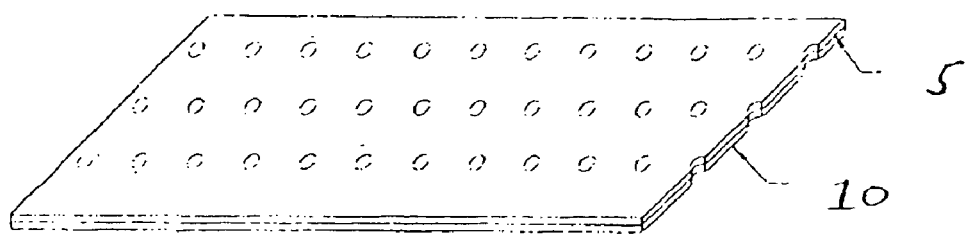
FIG. 9 is an illustration of a perforated embodiment of the present invention.
Figure 10:
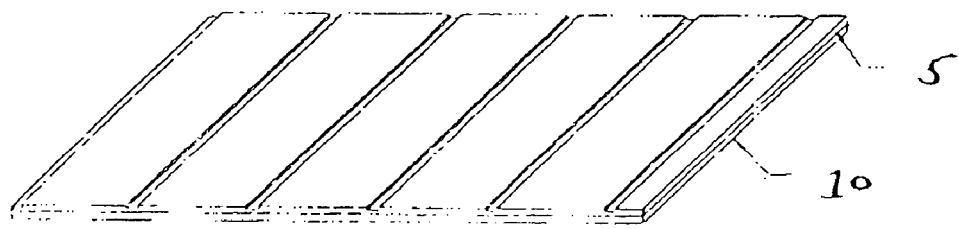
FIG. 10 is an embodiment illustrating gel layer 5 having surface imperfections provided in the form of parallel grooves.
Figure 11:
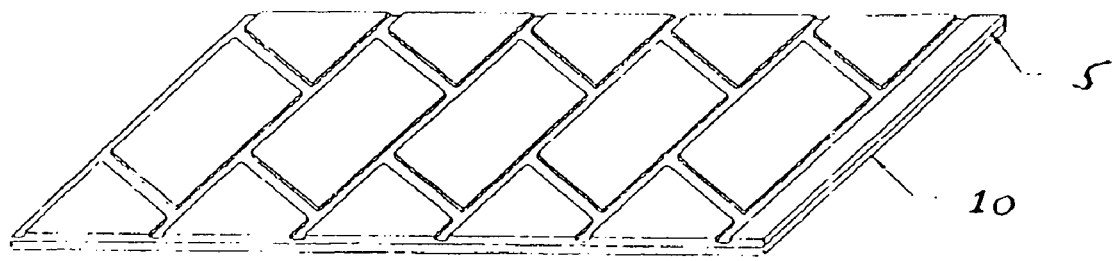
FIG. 11 is an embodiment illustrating gel layer 5 having surface imperfections provided in the form of a tread pattern of intersecting grooves.

In another embodiment, the gel layer may be provided with physical shape characteristics that provide greater comfort to the user. FIG. 9 illustrates a perforated composition. FIGS. 10 and 11 illustrate the gel layer having a series, or tread pattern, of grooves located on the surface of the gel layer that contacts the skin of the user. These surface imperfections, i.e. perforations and/or grooves, aid in directing moisture, such as sweat generated during use of the invention, to the outside of the wrap and away from the skin of the user. They also permit an amount of air to contact the skin within the treatment area. This reduces the amount of sweating in the treatment area caused by bandage use.

In another embodiment of the invention, an absorbent material providing a wicking effect can be incorporated into the composition of the wrap. The wicking material provides greater comfort to the user by wicking moisture, such as sweat, away from the skin of the user. This allows the treated area of the skin to remain dryer during use, and is more comfortable to the user.

The wicking material should be at least as stretchable and flexible as carrier 10 so that the properties of musculo-skeletal support and conformance to bodily contours are not significantly impaired by the incorporation of the wicking material. Polypropylene, cotton and nylon, for example, are some of the many known materials that are suitable for use as a wicking material in this invention.

Figure 12:
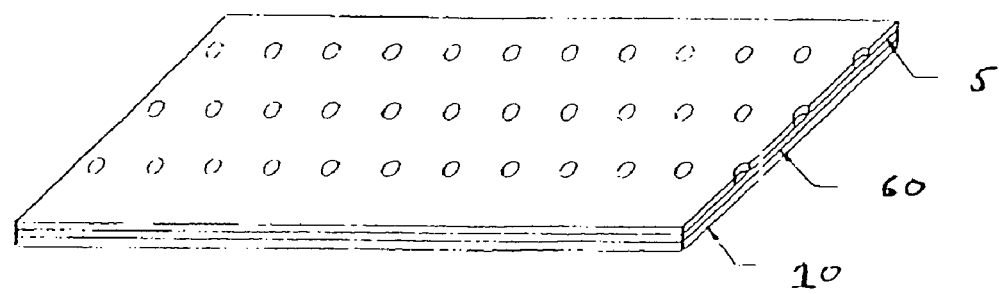
FIG. 12 is an embodiment illustrating a gel layer 5, a wicking layer 60 and a carrier 10.

An embodiment of the present invention combines the musculo-skeletal support and treatment benefits of the gel and carrier composition with the comfort provided by incorporation of a wicking material. In FIG. 12, a layer of wicking material 60 is sandwiched between the carrier 10 and gel 5. In this embodiment, gel layer 5 is perforated to provide greater migration of moisture away from the skin. It is not necessary, however, that the gel layer be perforated for wicking to occur. Moisture will migrate naturally through a solid gel layer. The perforation density, i.e. the number and/or size of perforations in the gel layer, may vary according to the particular requirements of the intended use of the bandage.

Figure 13:
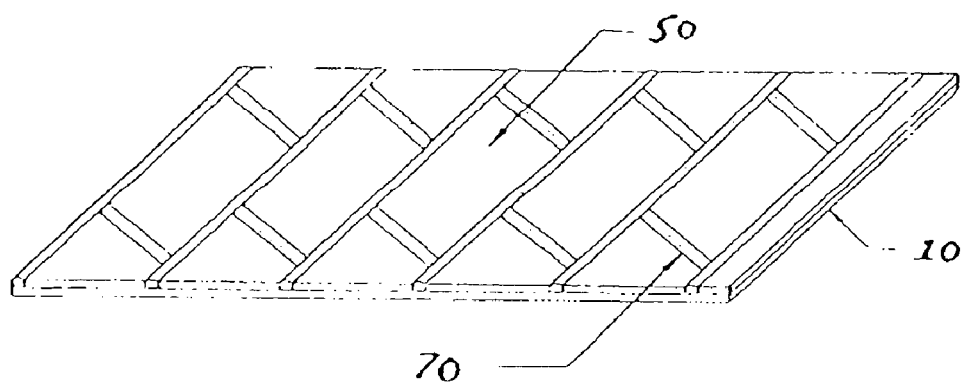
FIG. 13 is an embodiment illustrating gel areas 50, wicking material 70 and carrier 10.

In a preferred embodiment of the invention, referring to FIG. 13, the treatment surface of the bandage, i.e. the surface that is in contact with the skin, is a combination of gel areas 50 and areas of wicking material 70. Each of the gel areas 50 is surrounded by a border of wicking material 70. The structure may be similar to, for example, that of a relatively flattened honey-comb "web" made of wicking material with each of the cells of the "web" containing an amount of gel. The wicking material 70 of this embodiment is in compressed contact with the skin of the treatment area and allows for wicking of moisture away from the treatment area in three dimensions. The particular shape and size of the gel areas and borders of wicking material can vary according to the desired product use.

Referring to FIG. 9, wicking materials of another embodiment of the invention may be used in the manufacture of, and/or incorporated into carrier 10. Moisture that is generated in the treatment area of the skin that migrates through the gel 5 is drawn or wicked away from the gel, and skin, by action of the wicking material in the carrier 10. The wicking action may be increased by the perforation of the gel layer 5 which permits the wicking material of the carrier to more readily absorb moisture from the treatment area because the perforations provide a migration pathway that is less resistant than the solid gel layer.

The silicone gel provides an additional comfort factor of "coolness" against the skin, which is not diminished to any large degree by keeping the present invention in place for the required period. Because the present invention is comfortable, supportive, adaptable, stretchable, trimmable, usable on any joint or area of the body around which it can be wrapped, it is expected to result in higher patient compliance with the treatment.

Figure 14:
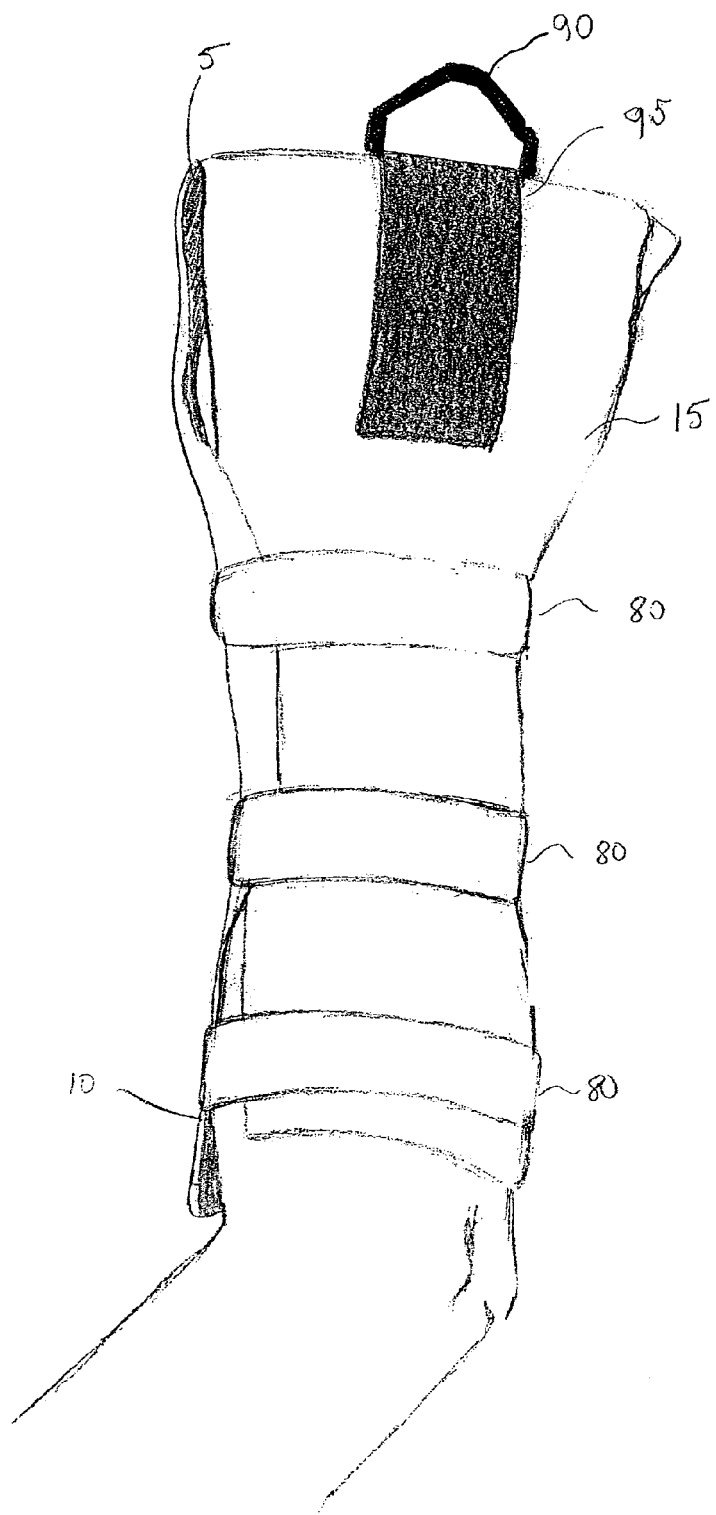
FIG. 14 is a perspective view of an embodiment illustrating the use of the sleeve for suspending an arm, showing loop surface 15 of carrier 10 and gel layer 5 of the wrap, closure strips 80, D-ring fastener 90, and distal pulling strip 95.
Figure 15:
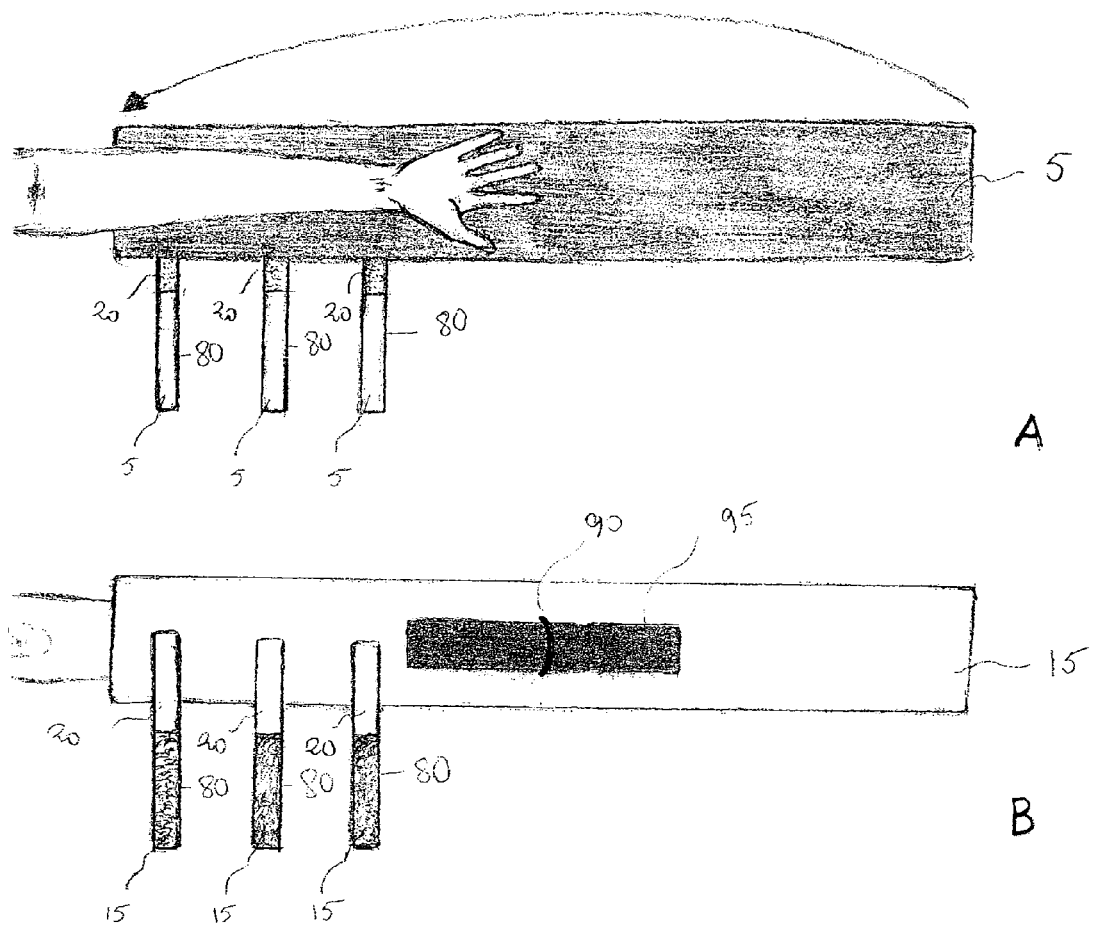
FIG. 15 is a perspective view of an embodiment illustrating the arm suspension sleeve as a single pre-assembled unit, showing the placement of the arm on the sleeve.
Figure 17:
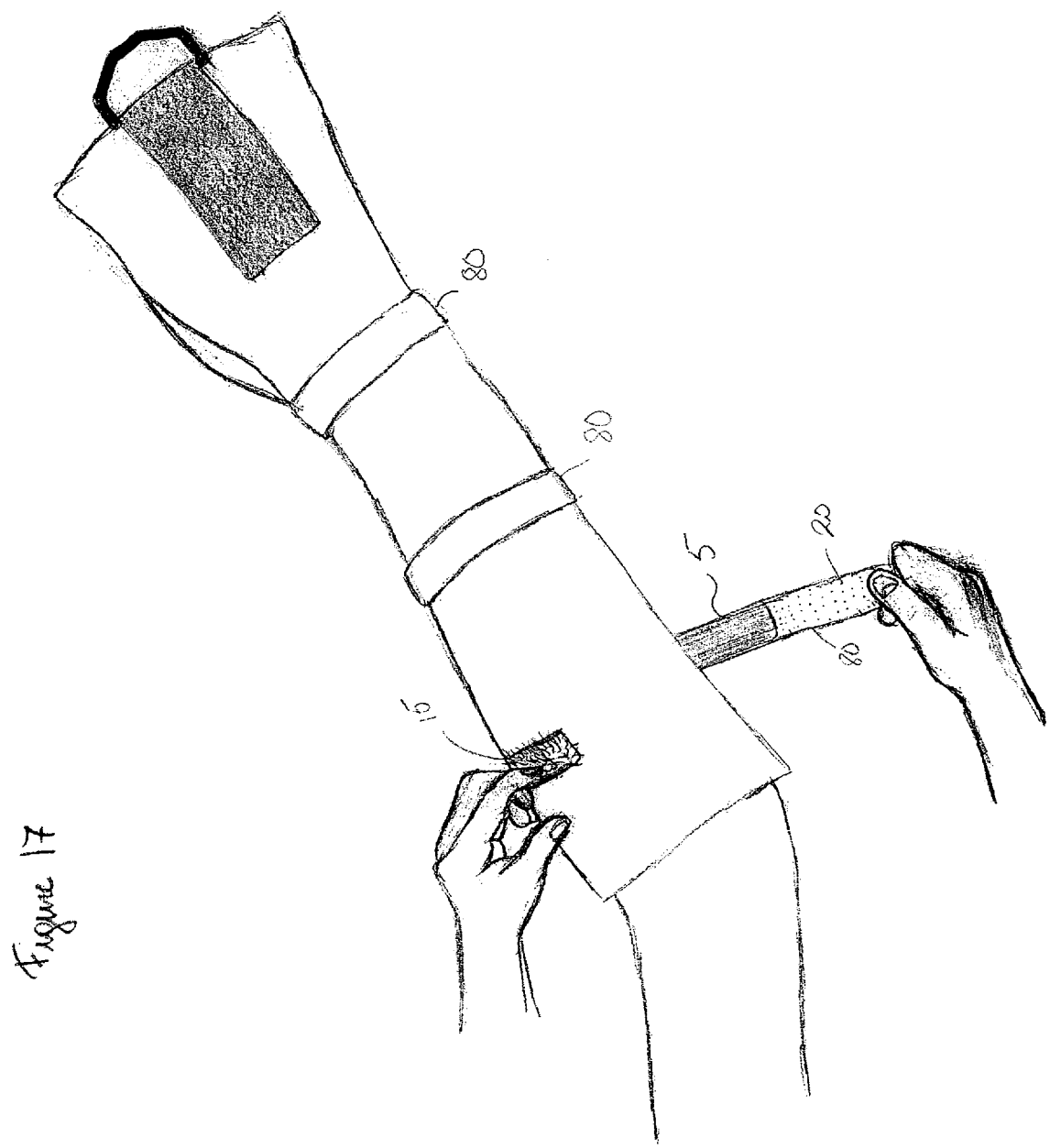
FIG. 17 is a perspective view of an embodiment illustrating the use of three closure strips 80 to secure the wrap around the arm. Two of these strips are shown already wrapped around the arm. The third one is shown during wrapping to illustrate that each closure strip consists of two strips, the first strip with a loop surface 15 and gel layer 5 opposite the loop surface, and the second strip having hook surface 20, which is attached to the loop surface 15 of the first strip to increase or decrease the length of the closure strip.
Figure 18:
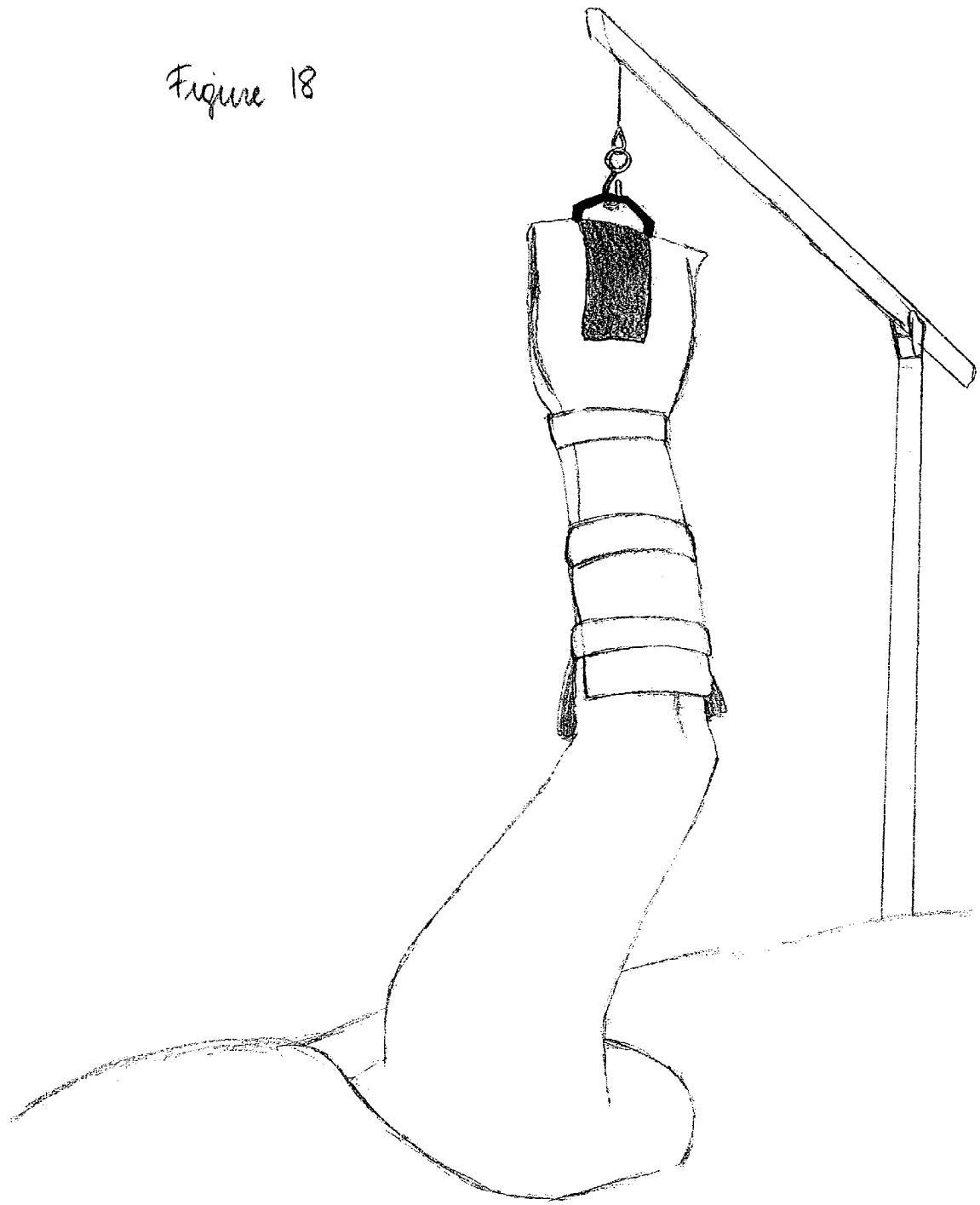
FIG. 18 is a perspective view of an embodiment illustrating the use of a sleeve for suspending an arm, showing the sleeve wrapped around the arm, and suspended from a suspension structure. The body of the patient is partially shown here laying on his or her side.

Another embodiment is a sleeve for suspending an arm during surgery, for example during arthroscopic surgery of the elbow or shoulder. For this embodiment, the wrap is placed around the arm, as shown in the embodiments of FIGS. 14, 17, 18, 19, and 20 so that the wrap encloses the arm longitudinally, with the gel layer 5 in contact with the skin and the loop side 15 of the supportive carrier 10 on the opposite side, as illustrated in the embodiments of FIGS. 14 and 15. FIG. 15 shows how the arm is longitudinally enclosed by the wrap to achieve the final position shown in FIGS. 14, 18, 19 and 20. The arm is placed on the gel layer 5, with the distal end of the hand resting on or about the longitudinal center of the wrap, as seen from the top in FIG. 15 A. As used herein, distal and proximal are used in reference to the shoulder, wherein the farthest point away from the shoulder is the distal end, and the closest point to the shoulder is the proximal end. The wrap is then folded longitudinally over the top of the arm in the direction of the arrow, using the distal end of the hand as the folding axis, and making the distal and proximal ends of the wrap approximately meet. The lateral edges of the wrap may then be tucked around the perimeter of the arm (not shown in the figure). The wrap is secured around the arm with one or more closure strips 80. The number, width and placement of the strips can vary as long as the wrap can be adequately secured around the arm. In the embodiment shown in FIG. 15, three closure strips are used. As shown in FIG. 15B, which is the view from the bottom of FIG. 15A, the opposite side to the gel layer 5 of the wrap, the loop side 15, has three closure strips 80 attached. Also attached to the loop side of the wrap is a D-ring fastener 90 by means of a distal pulling strip 95. Once the wrapping is completed, the wrapped arm is suspended by the D-ring fastener 90 from a holding structure. As used here, a holding structure is a device to which the wrapped arm can be attached, and which is able to keep the arm in a particular position. As used here, examples of a holding structure are suspension structures and traction structures. In a suspension structure, the wrapped arm is hanging from the structure, as shown in FIG. 18. A suspension structure is typically used during arthroscopic surgery. When the wrapped arm is suspended from a traction device, a pulling force is actively applied away from the wrapped arm. A traction device is typically used during post-operative recovery. Typically, a holding structure will be a vertical structure heavy enough to firmly hold the weight of the wrapped arm, with different transverse structures attached, the position of which can be changed without the whole structure losing stability. Examples of holding structures are well known to those of skill in the art.

Each closure strip may consist of two strips which are releasably attached to each other to change the length of the closure strip, typically to increase the length. One strip can be the non-stretchable hook portion 20 of a hook and loop fastener (the "hook strip"). The other strip can be the stretchable loop portion of a hook and loop fastener (the "loop strip"). To firmly secure the wrap around the arm, the hook strip can be attached to the loop side of the wrap. The loop strip is then slightly stretched while both strips, which are attached to each other in one continuous strip, are wrapped around the arm. The free end of the loop strip can then be attached to the end of the hook strip already attached to the wrap by detaching a short stretch of the free end of the hook strip. Attaching the hook strip to the loop surface 15 of the wrap is not necessary for securing the wrap around the arm. The closure strip may be only attached to itself in order to secure the wrap appropriately. As shown in the embodiment of FIG. 17, the free end of the loop strip can be held on the wrap while the loop strip is slightly stretched by pulling from the end of the hook strip attached to the loop strip. The free end of the hook strip can then be wrapped around the arm and attached to the loop strip, securing the wrap to the arm effectively yet comfortably. The same process can be done by holding the free end of the hook portion of the strip on the wrap, and wrapping the loop portion around the arm. The stretchable loop strip has the added advantage of providing additional adjusting length, allowing the closure strip to fit around arms of different sizes without the need of customizing the size of the closure strips.

Figure 16:
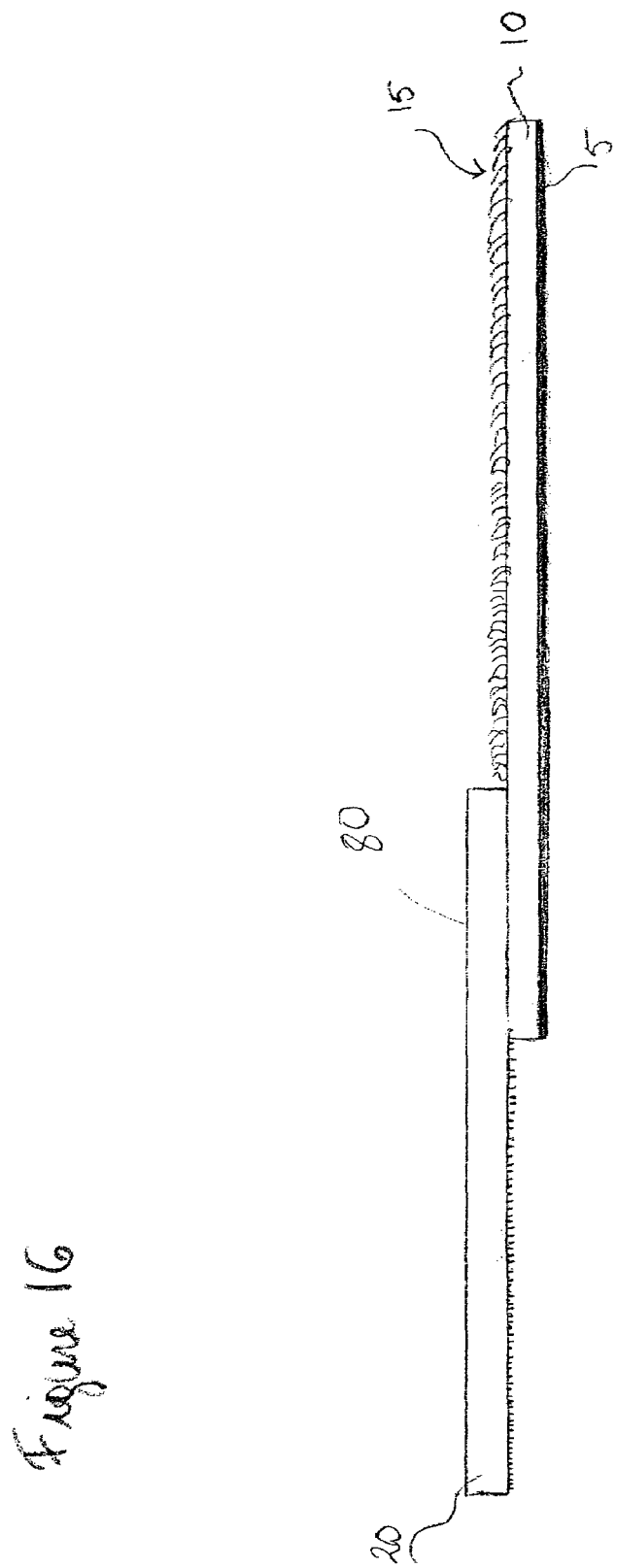
FIG. 16 illustrates a two part closure strip 80 consisting of two strips, which are attached to each other to adjust the length of the closure strip. The first strip has a loop surface 15, a supportive carrier 10, and gel layer 5 opposite the loop surface, and a second strip having a hook surface 20 for attaching to the loop surface of the first strip.

In another embodiment shown in FIGS. 15, 16, and 17, the stretchable loop strip can be coated with gel layer 5 on the side opposite to the "fuzzy" side 15 of the carrier 10. The opposite side to the "fuzzy" side may come in contact with the skin, depending on the size of the arm to be wrapped and the way in which the closure strip is wrapped around the arm. The gel surface of the loop strip may come in contact with the skin of the arm only when the loop surface of the loop strip is wrapped facing away from the loop surface of the wrap. In the event the loop strip comes in contact with the skin, the gel lining of the strip will help resisting slippage of the strip and decrease the potential skin irritation caused by prolonged pressure of the strip on the skin.

In other embodiments, closure strips can be made of other materials or fabrics such as nylon, cotton, leather, etc . . . , as long as they can secure the wrap around the arm effectively.

Figure 19:
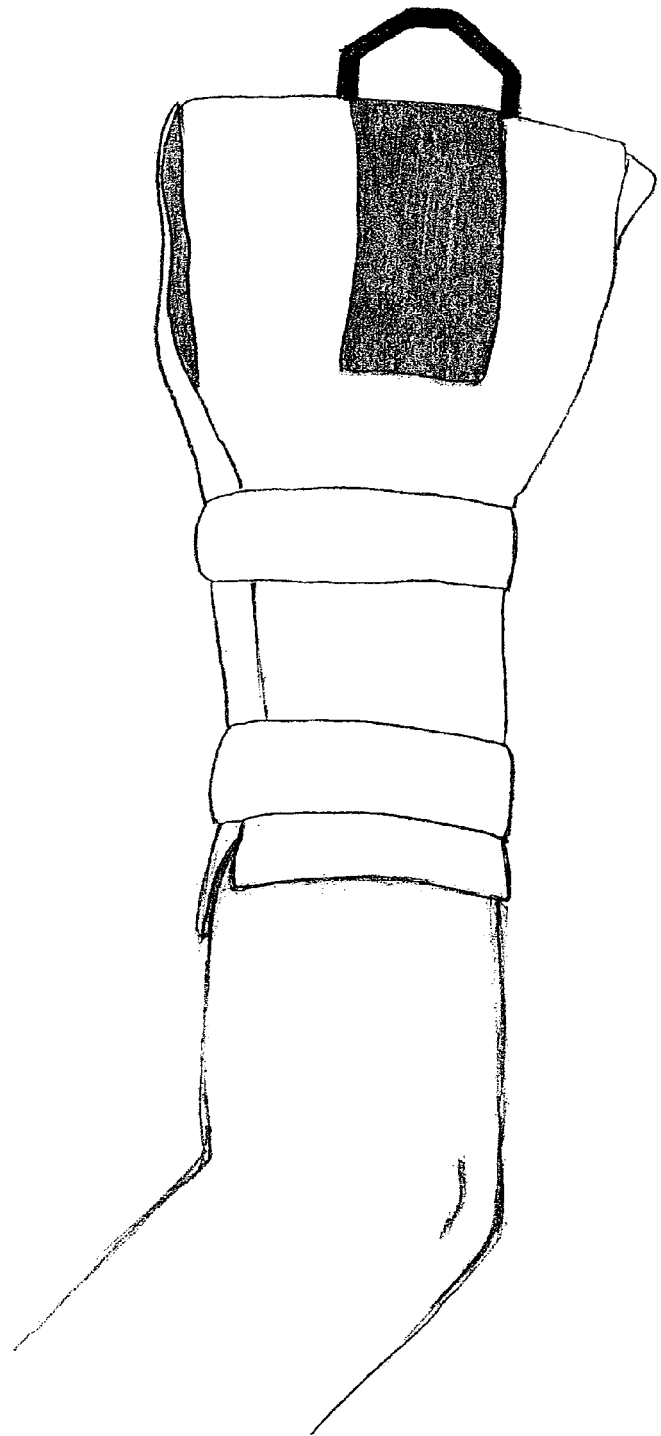
FIG. 19 is a perspective view of an embodiment illustrating a sleeve for suspending an arm for elbow surgery.
Figure 20:
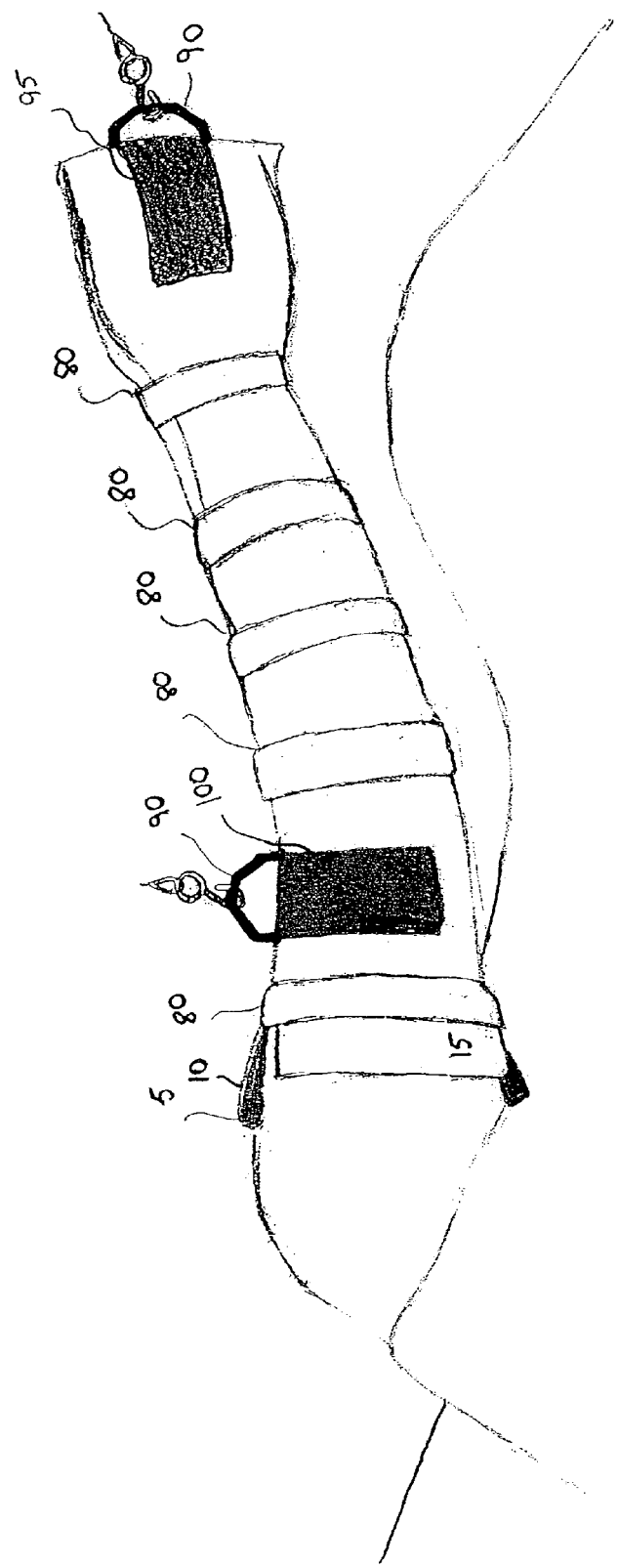
FIG. 20 is a perspective view of an embodiment illustrating a sleeve for suspending an arm with a distal pulling force exerted from the distal pulling strip 95 to keep the arm extended, and a proximal pulling force exerted from the proximal pulling strip 100 to elevate the arm. Also shown are loop surface 15 of carrier 10 and gel layer 5 of the wrap, closure strips 80, and D-ring fasteners 90. The body of the patient is partially shown here laying in the lateral decubitus position.
Figure 21:
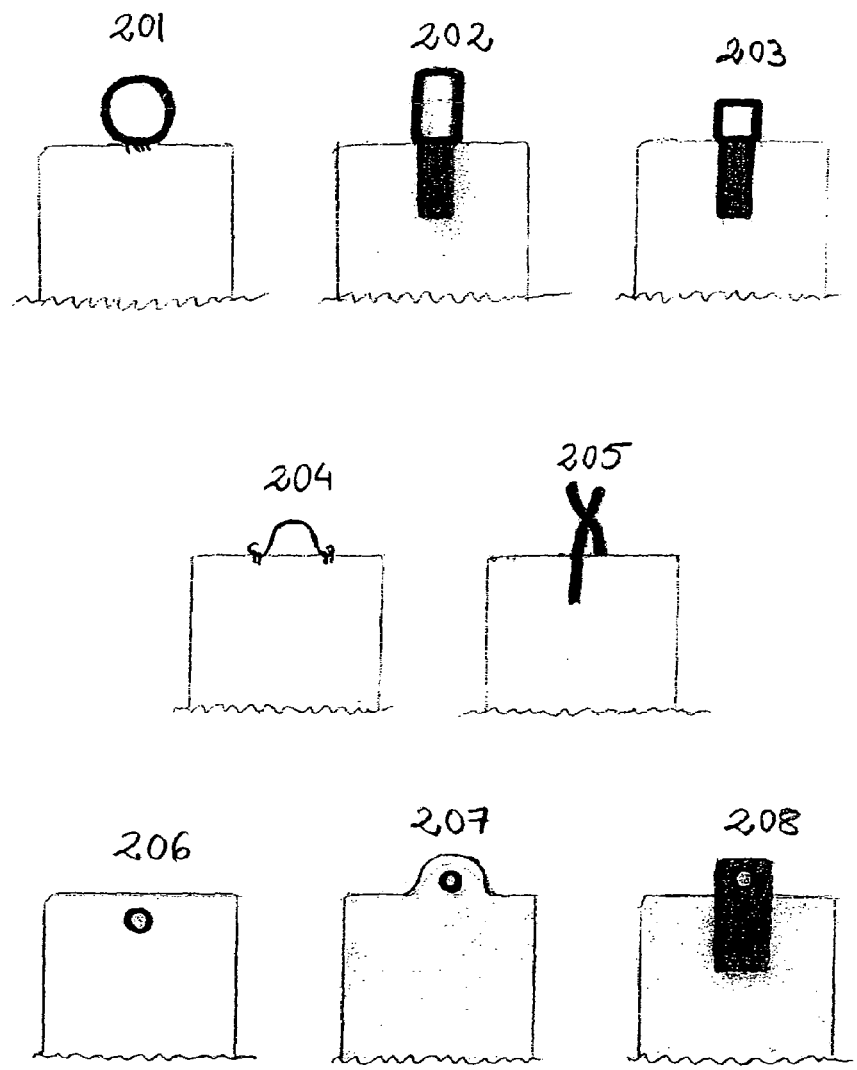
FIG. 21 shows different fasteners and how they can be attached to the wrap, which is partially represented here as being already folded. These fasteners are: a circular ring 201, a rectangular ring 202, a square ring 203, an open ring with built-in-hooks 204, cloth straps, built-in perforation in the wrap 206, perforation in an extension of the wrap 207, and perforation in a pulling strip 208. Fasteners in 201, 204 and 205 are sewn to the wrap, fasteners in 202, 203 and 208 are attached by means of a pulling strip. The curved line indicates only a part of the wrap is shown.

In a further embodiment, the fastener from which the sleeve is suspended is a D-ring 90, as shown in FIGS. 14 to 20. However, other fasteners can be used as shown in FIG. 21, such as a circular ring 201, a rectangular ring 202, a square ring 203, or an open ring with built-in-hooks 204, among others. These rings can be made of plastic, metal or other materials; however, cloth straps 205 that can be knotted to a holding structure can also be used. Multiple fasteners may also be used, depending on the weight of the arm to be suspended, and the particular position in which the arm is to be held.

The fastener can be attached to the outside surface of the wrap in a fixed or removable position. One way to attach the fastener in a fixed position is by sewing it to a fixed position as shown in embodiments 201, 204, and 205 of FIG. 21. Other means to attach the fastener to a fixed position may be by using buttons, hook and eyes, etc . . . , as long as they can sustain the weight of the arm. Removably attaching each fastener to the loop side of the wrap with one or more pulling strips as shown in FIGS. 14, 15, 17, 18, 19, and 20, and in embodiments 202 and 203 of FIG. 21 is also suitable.

The pulling strip can be the non-stretchable hook portion 20 of a hook and loop fastener. It can therefore be easily attached to the outside of the wrap when the supportive carrier is the loop portion of a hook and loop fastener. In other embodiments the pulling strip(s) can be made of other materials or fabrics, such as described above for the closure strips, which can then be attached to the wrap by means such as adhesives, sewing, etc. . . . Alternatively, one perforation or more can be made in the wrap so that the wrap can be directly suspended from a holding structure. Embodiments 206 and 207 with such perforations are shown in FIG. 21. In another embodiment 208 as shown in FIG. 21, the perforation can be made in a pulling strip.

In one embodiment, the sleeve is suspended by a single fastener that is attached to the longitudinal center of the wrap, as shown in FIGS. 14 to 19. This fastener will be used for distal pulling from the shoulder. If additional fasteners are needed to suspend the wrapped arm, they will be placed in such a way to most effectively distribute the weight of the arm among the different fasteners. In another embodiment as illustrated in FIG. 20, an additional fastener is used at the proximal part of the wrap, that part of the wrap pulling from the shoulder in a perpendicular orientation. This allows manipulation and modification of the direction of the angle of suspension of the arm. For this embodiment, the fastener is attached to the wrap in the same orientation as the closure strips, i.e., perpendicularly with respect to the arm. This additional fastener can be a D-ring that is attached to the wrap by means of a proximal pulling strip 100 made of the hook portion 20 of a hook and loop fastener, which can be easily and removably attached to the loop portion of the wrap. In other embodiments, other fasteners can be used as described above. These fasteners can also be attached to the wrap in different ways as described above. Perforations in an extension of the wrap to directly suspend the wrap can also be used.

In other embodiments, the carrier in the wrap can be a non-stretchable material or fabric such as cotton velours, nylon, linen, etc . . . as long as it can effectively sustain the weight of the arm.

In one embodiment, the gel layer 5 in the suspension sleeve may have surface imperfections, i.e. perforations and/or grooves, earlier described in FIGS. 9, 10, and 11, to aid in directing moisture, such as sweat generated during use of the sleeve, to the outside of the wrap and away from the skin. In another embodiment, an absorbent material providing a wicking effect can be incorporated into the composition of the wrap, as described in FIGS. 12 and 13.

In one embodiment, the sleeve can be prepared in long sheets of a fixed length that will be suitable for properly enclosing arms having different circumferences and lengths. The fastener, closure strips, and distal pulling strip can then be removably attached to the same positions on the wrap, allowing pre-assembly or minimal assembly prior to surgery. For this embodiment, a length can be determined for shoulder surgery, which will enclose most of the forearm. For example, for shoulder surgery, the dimension of the wrap will typically be 6"×34". For elbow surgery, a shorter length will be required, as shown in FIG. 19, since the area around the elbow must be accessible to the surgeon. For elbow surgery, the dimension of the wrap will typically be 6"×24". If needed, the precut wrap sheet for shoulder or elbow can be easily customized by trimming the length or width of the wrap with scissors or other standard cutting means.

Typically, the wrap will be in the form of a roll or a pre-cut sheet, but in one embodiment, the wrap can also be presented in the form of a shirt sleeve of varying lengths. Namely, the wrap can be presented in the folded form, and stitched on the lateral edges, leaving one free end to insert the arm. This form can also be achieved by stitching two sheets of wrap together along the lateral edges and the distal end, leaving one free end to insert the arm.

When the sleeve is to be used for elbow surgery, it will typically have two closure strips, as shown in FIG. 19. Nonetheless, adjustments can be made depending on the width of the strips used and the length of the forearm to be wrapped.

Figure 5:
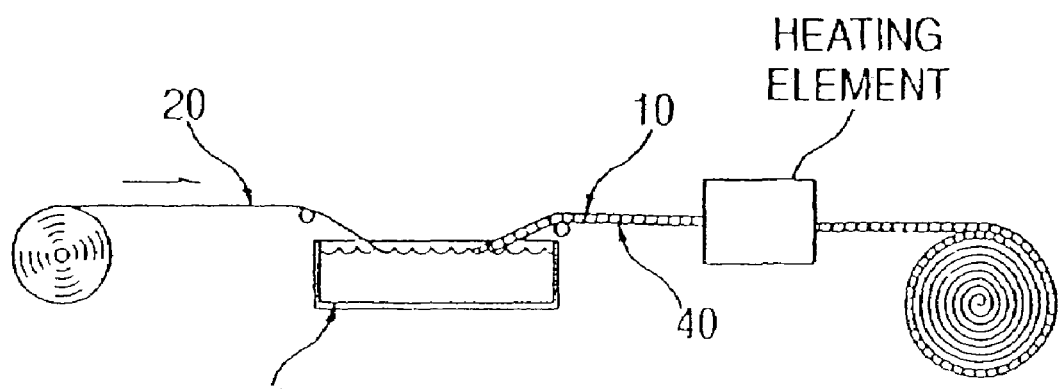
FIG. 5 illustrates a method of manufacture using gel bath 30 and carrier 10

A method of manufacturing the present invention is shown in FIG. 5, and described as follows.

The desired gel is mixed as designated by the material manufacturer, i.e. 1:1, 3:1, or 10:1 parts resin and catalyst, although the mixture can be varied to obtain different degrees of tack from the final cured gel. The mixture is poured onto a flat surface, such as large sheet of polycarbonate, and allowed to settle until it is a consistent thickness. The gel, after having been allowed to settle, has a consistent thickness and is surrounded by an appropriate sized wall to contain the gel on the polycarbonate surface. In one embodiment, the gel thickness is approximately 2 mm, although the thickness may vary from as little as 0.5 mm up to 4 mm. Meanwhile, the carrier 10 may be washed in a mild soapy solution such as Ivory® soap to remove the oils and agents used in processing the fabric, and allowed to air dry. After the gel is settled to a consistent thickness (about 20-60 minutes) the dry carrier 10 is placed on top with the loop surface of the carrier 10 away from the gel. The assembled materials are then allowed to cure. In a preferred embodiment, the combined gel and carrier 10 are placed in a curing oven for 1-3 hours and at a temperature of about 100 to 180 degrees centigrade until the gel is cured. The specific time and temperature of the curing process can be determined based on the type of gel composition and the desired cured properties of the bandage. The appropriate curing temperature and curing time can then be varied accordingly. The cured, assembled materials are then removed from the oven and can then be cut into any shape desired.

The present invention also lends itself well to mass production by coextrusion as shown in FIG. 5. In this embodiment, stretchable carrier 10 is continuously unrolled from a large roll of material onto a bath 30 of gel. As the carrier 10 is removed from the bath 30 a layer of gel 40 adheres to the carrier 10 and settles to a uniform thickness. The stream of combined carrier/gel is then passed through a heating oven and cured. At the other end of the oven are take-up rolls and/or cutting fixtures to facilitate rolling or cutting the cured product into any desired configuration.

Figure 6:
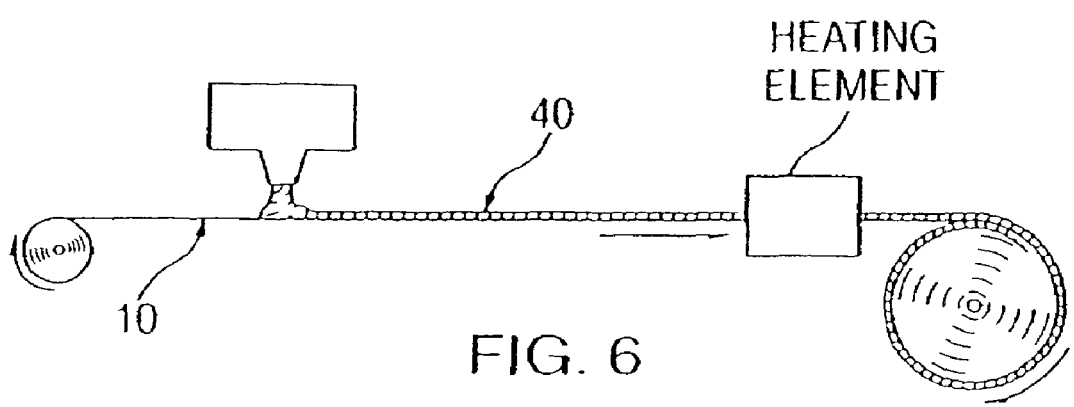
FIG. 6 illustrates river of carrier 10 and uncured gel compound 40.

In another embodiment shown in FIG. 6, an amount of gel 40 is deposited onto a river of carrier 10 as the carrier 10 passes beneath the gel. A layer of gel is formed on the side of the carrier 10 opposite the loops and the gel is allowed to settle to a uniform thickness. The river of combined carrier/gel material is then passed through a heating oven and cured. At the other end of the oven are take-up rolls and/or cutting fixtures to facilitate rolling or cutting the cured product into any desired configuration.

Using either of the previous embodiments, there are specific production techniques which will result in a consistent layer of gel being applied to the flat side of the stretch carrier 10, opposite the loop side.

What is claimed is:

1. A suspension sleeve for an arm comprising:
   a) a supportive wrap having an outer surface and an inner surface, which wrap comprises a gel layer having a skin contacting surface and an opposite adhesion surface and a supportive carrier layer having an outer surface and an opposite adhesion surface, with the adhesion surfaces bonded together to form the supportive wrap;
   b) one or more closure strips of a material suitable for releasably securing the longitudinally folded wrap around the arm; and
   c) a suspending means at about the longitudinal mid-point of the wrap for attaching the wrapped arm to a holding structure.

2. The sleeve of claim 1, wherein the gel is a silicone gel.

3. The sleeve of claim 2, wherein the silicone gel is a cured diorganosiloxane.

4. The sleeve of claim 2, wherein the gel layer contains surface imperfections.

5. The sleeve of claim 4, wherein the surface imperfections are grooves or perforations.

6. The sleeve of claim 2, wherein the wrap further comprises a moisture wicking material in contact with the gel layer and the supportive carrier layer, which material is incorporated into the carrier layer or is sandwiched between the gel layer and the carrier layer.

7. The sleeve of claim 1, wherein the supportive carrier is the stretchable loop portion of a hook and loop fastener.

8. The sleeve of claim 7, wherein the suspending means comprises a fastener and a distal pulling strip attachable to the outer surface of the wrap at about the longitudinal middle.

9. The sleeve of claim 8, wherein the suspending means further comprises a fastener and a proximal pulling strip attachable to the outer surface of the wrap near the proximal end of the wrap.

10. The sleeve of claim 8 or 9, wherein the fastener is selected from the group consisting a ring, a hook, and a strap.

11. The sleeve of claim 9, wherein the distal and/or proximal pulling strips are the hook portion of a hook and loop fastener.

12. The sleeve of claim 7, wherein the suspending means is a perforation in the wrap or a perforation in a distal and/or a proximal pulling strip.

13. The sleeve of claim 1, wherein the one or more closure strips comprise (i) a non-stretchable hook portion of a hook and loop fastener and (ii) a stretchable loop portion of a hook and loop fastener, with the non-stretchable hook portion overlapping and being releasably attached to the stretchable loop portion.

14. The sleeve of claim 1, wherein the one or more closure strips comprise (i) the non-stretchable hook portion of a hook and loop fastener, (ii) the stretchable loop portion of a hook and loop fastener, and (iii) the non-stretchable hook portion of a hook and loop fastener, wherein the non-stretchable hook portions are releasably attached to the ends of the stretchable loop portion.

15. The sleeve of claim 1, wherein the one or more closure strips comprise (i) the stretchable loop portion of a hook and loop fastener, (ii) the non-stretchable hook portion of a loop fastener, and (iii) the stretchable loop portion of a hook and loop fastener, wherein the stretchable loop portions are releasably attached to the ends of the non-stretchable hook portion.

16. The sleeve of claim 13, 14, or 15, wherein the non-loop surface of the stretchable loop portion is coated with a gel.

17. The sleeve of claim 16, wherein the gel is a silicone gel.

18. The sleeve of claim 17, wherein the silicone gel is a cured diorganosiloxane.

19. The sleeve of claim 1, wherein the one or more closure strips and/or suspending means are releasably attached to the outer surface of the wrap.

20. The sleeve of claim 1, wherein the holding structure is a suspension device or a traction device.

21. A suspension sleeve for an arm comprising:
a) a supportive wrap having an outer carrier surface and an inner gel surface, which wrap comprises a gel layer having a skin contacting surface and an adhesion surface opposite the skin contacting surface and a supportive carrier layer which is the stretchable loop portion of a hook and loop fastener which carrier layer has a loop outer surface and an opposite adhesion surface, the adhesion surfaces being bonded together to form the supportive wrap;
b) one or more closure strips of a material suitable for securing the longitudinally folded wrap around the arm,
c) a non-stretchable or stretchable distal pulling strip releasably attachable at about the longitudinal midpoint of the outer surface of the wrap, which distal pulling strip is the hook portion of a hook and loop fastener; and
d) a D-ring attached to about the mid-point of the distal pulling strip for suspending the wrapped arm from a suspension structure or a traction structure.

22. The sleeve of claim 21, wherein the one or more closure strips are releasably attached to the outer surface of the wrap.

23. The sleeve of claim 22, wherein the one or more closure strips comprise (i) the non-stretchable hook portion of a hook and loop fastener and (ii) the stretchable loop portion of a hook and loop fastener, with the non-stretchable hook portion overlapping and releasably attached to the stretchable loop portion.

24. The sleeve of claim 1 or 21, for use in suspending the arm during surgery.

25. The sleeve of claim 24, wherein the surgery is arthroscopic shoulder or elbow surgery.

* * * * *